(12) United States Patent
Ryu et al.

(10) Patent No.: US 10,973,378 B2
(45) Date of Patent: Apr. 13, 2021

(54) PORTABLE URINAL

(71) Applicants: Sidae Ryu, Seoul (KR); Ryeongmo Ryu, Seoul (KR); Ryeongmin Ryu, Seoul (KR)

(72) Inventors: Sidae Ryu, Seoul (KR); Ryeongmo Ryu, Seoul (KR); Ryeongmin Ryu, Seoul (KR)

( * ) Notice: Subject to any disclaimer, the term of this patent is extended or adjusted under 35 U.S.C. 154(b) by 395 days.

(21) Appl. No.: 16/081,923

(22) PCT Filed: Mar. 7, 2017

(86) PCT No.: PCT/KR2017/002422
§ 371 (c)(1),
(2) Date: Sep. 3, 2018

(87) PCT Pub. No.: WO2017/155264
PCT Pub. Date: Sep. 14, 2017

(65) Prior Publication Data
US 2019/0059662 A1    Feb. 28, 2019

(30) Foreign Application Priority Data

Mar. 8, 2016 (KR) .................. 10-2016-0027476
Mar. 6, 2017 (KR) .................. 10-2017-0028120

(51) Int. Cl.
*A47K 11/12* (2006.01)
*A47K 11/06* (2006.01)
(Continued)

(52) U.S. Cl.
CPC .............. *A47K 11/12* (2013.01); *A47K 11/06* (2013.01); *A61F 13/15252* (2013.01);
(Continued)

(58) Field of Classification Search
CPC ......... A47K 11/12; A47K 11/06; A61F 5/451; A61F 5/4556; A61F 5/5121;
(Continued)

(56) References Cited

U.S. PATENT DOCUMENTS 4,882,794 A * 11/1989 Stewart, III ........... A61G 9/003
4/451
5,752,946 A * 5/1998 Boberg ............... A61F 13/4758
604/385.24
(Continued)

FOREIGN PATENT DOCUMENTS

JP          06-005614 U    1/1994
JP        2001-245921 A    9/2001
(Continued)

OTHER PUBLICATIONS

International Search Report for PCT/KR2017/002422 dated Jul. 10, 2017 from Korean Intellectual Property Office.

*Primary Examiner* — Tatyana Zalukaeva
*Assistant Examiner* — Heather K Barnwell
(74) *Attorney, Agent, or Firm* — Revolution IP, PLLC

(57) ABSTRACT

A portable urinal includes: a moisture solidification layer containing a super absorbent polymer; and a plate-shaped support member supporting the moisture solidification layer and having a hollow portion; and a shape retaining wire retaining the plate-shaped support member in the form of an alphabet "C", wherein the shape retaining wire has a single closed curve in the form of covering the plate-shaped support member and is provided along the edge of the plate-shaped support member.

3 Claims, 4 Drawing Sheets

(51) Int. Cl.
    *A61F 13/15*    (2006.01)
    *A61F 13/472*    (2006.01)
    *A61F 13/47*    (2006.01)

(52) U.S. Cl.
    CPC ........ *A61F 13/472* (2013.01); *A61F 13/4702* (2013.01); *A61F 2013/15146* (2013.01); *A61F 2013/15463* (2013.01)

(58) Field of Classification Search
    CPC ............ A61F 2013/15146; A61F 5/453; A61F 5/455; A61G 9/00
    See application file for complete search history.

(56) References Cited

U.S. PATENT DOCUMENTS

| | | | | |
|---|---|---|---|---|
| 5,852,830 | A | * | 12/1998 | Horn ...................... A47K 11/12 |
| | | | | 4/144.1 |
| 2001/0021836 | A1 | | 9/2001 | Kashiwagi |
| 2007/0214553 | A1 | * | 9/2007 | Carromba ............. A61F 5/4556 |
| | | | | 4/144.4 |
| 2008/0132861 | A1 | * | 6/2008 | Tomes ................... A61F 13/15 |
| | | | | 604/367 |

FOREIGN PATENT DOCUMENTS

| | | | |
|---|---|---|---|
| JP | 5241597 B2 | * | 7/2013 |
| JP | 5241597 B2 | | 7/2013 |
| JP | 5581088 B2 | | 8/2014 |
| KR | 20-0478064 Y1 | | 8/2015 |

\* cited by examiner

【Figure 1】
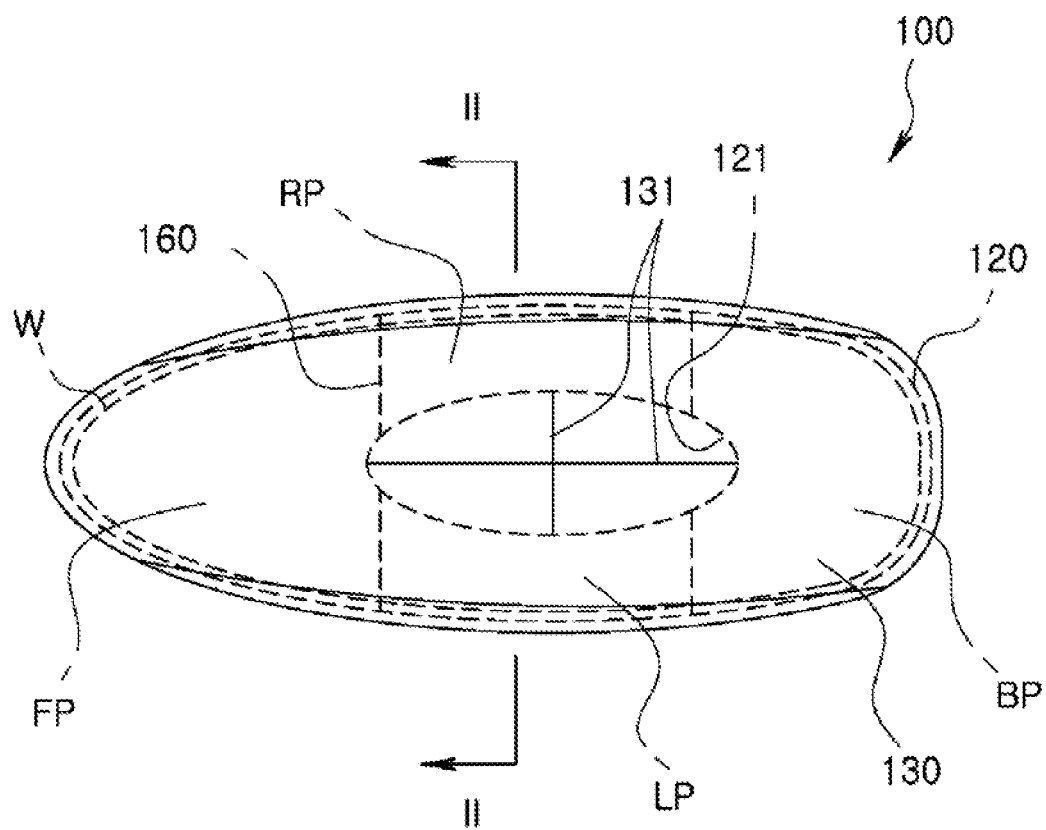
【Figure 2】
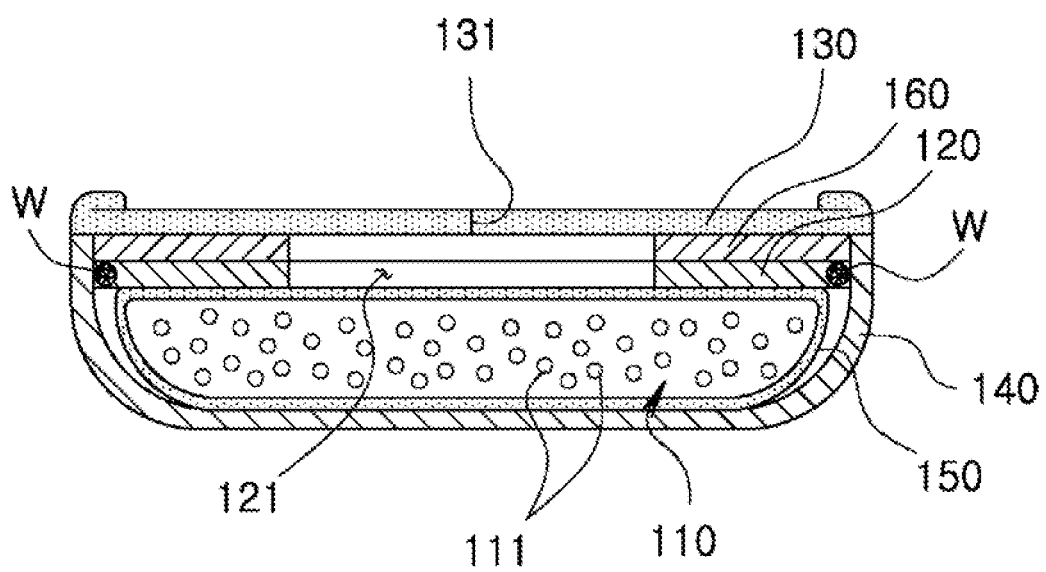

[Figure 3]
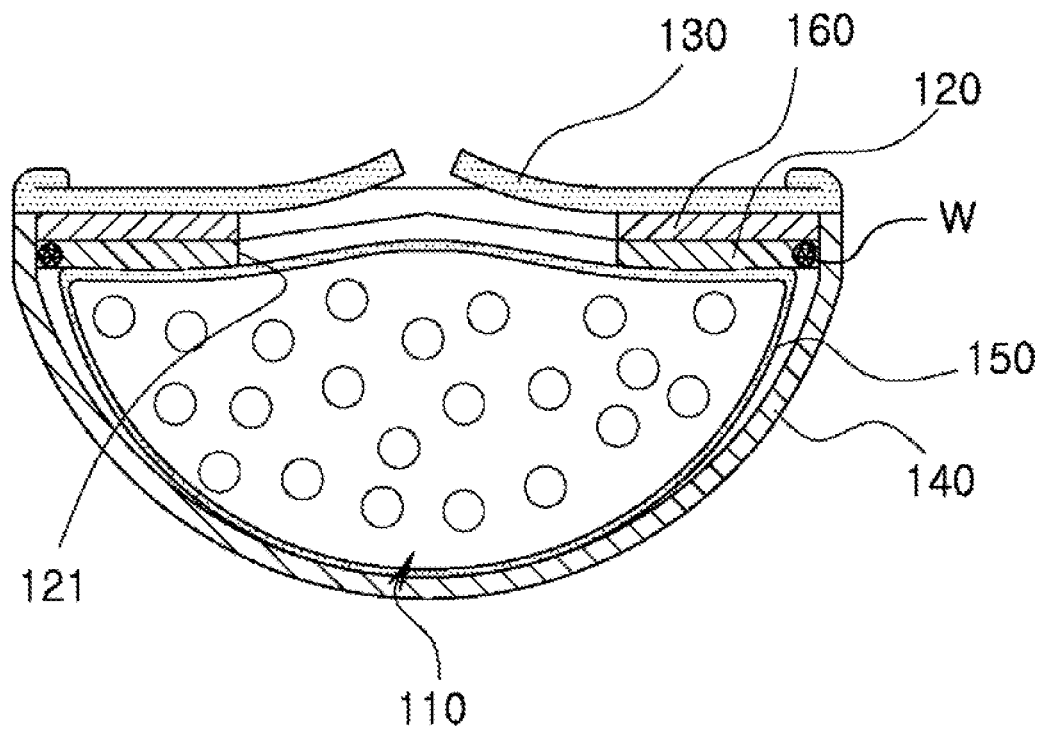
[Figure 4]
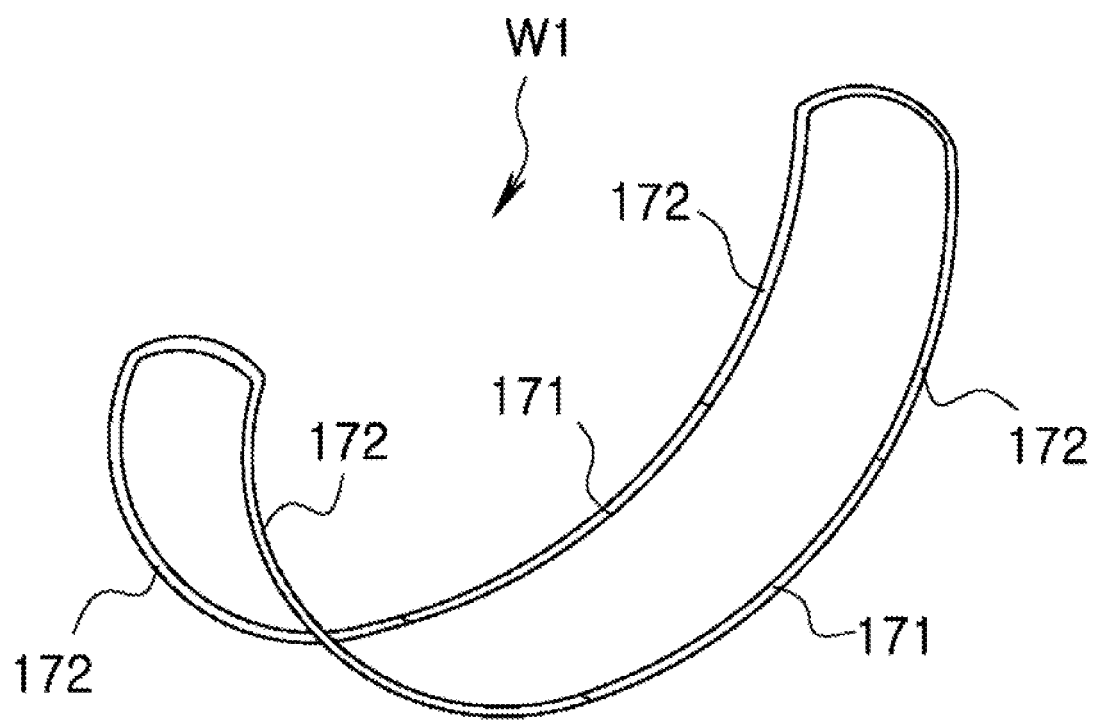

[Figure 5]
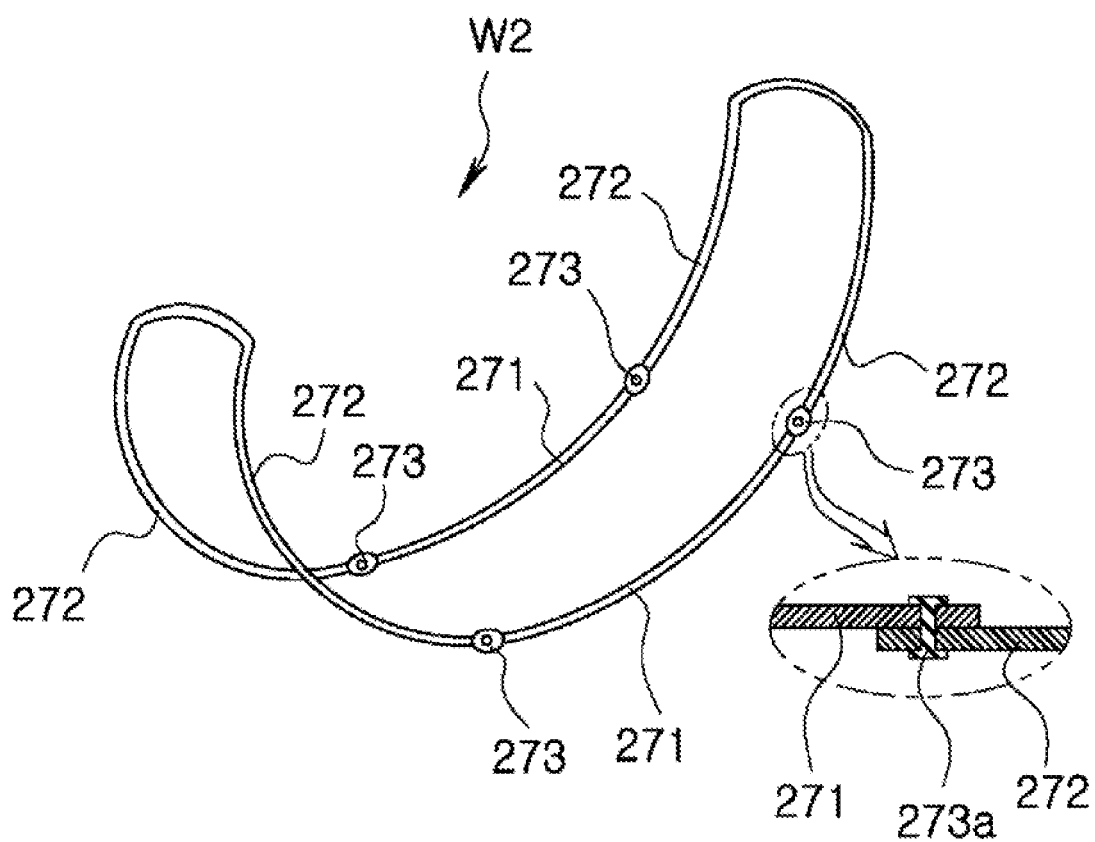

[Figure 6]
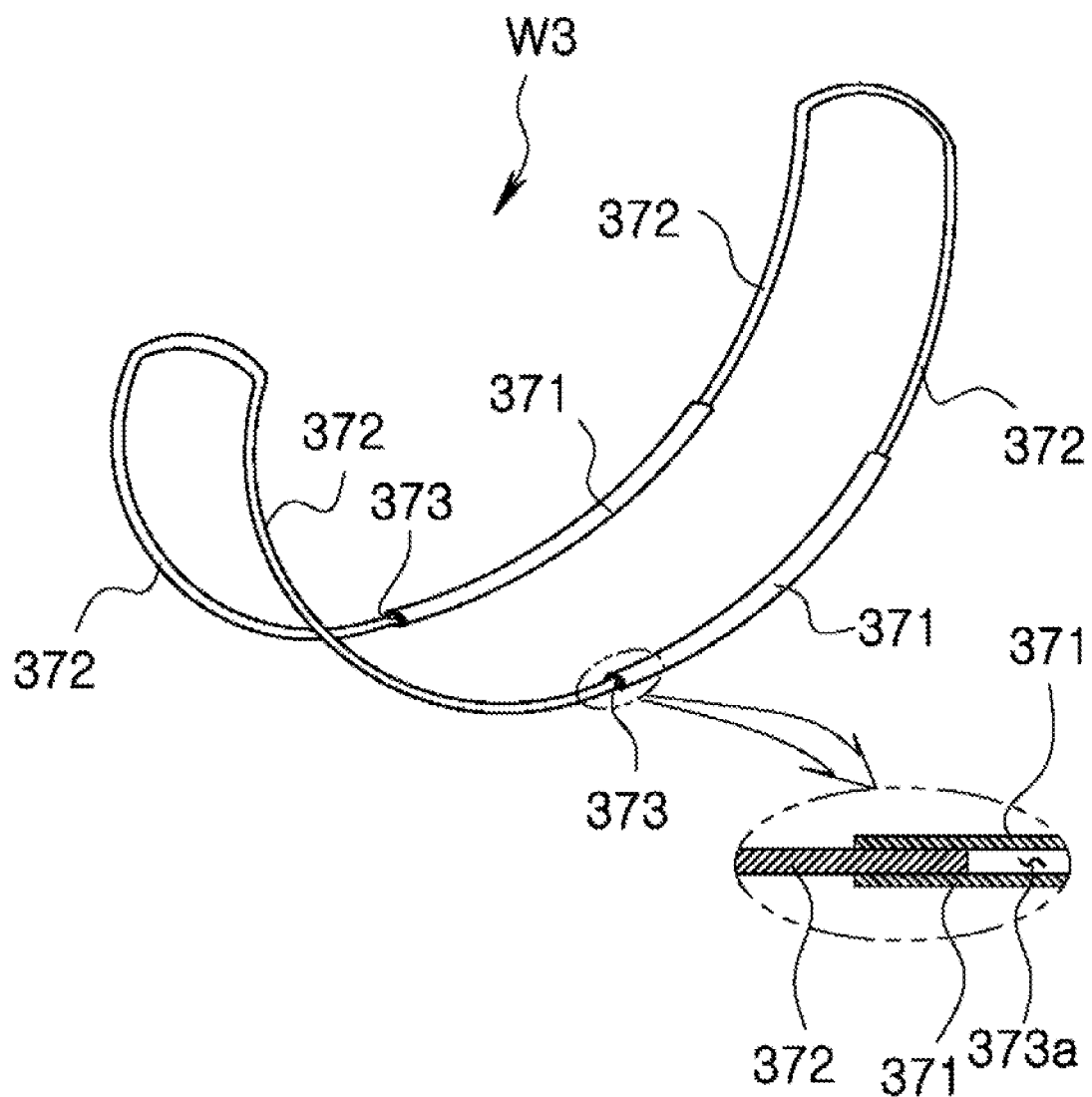

PORTABLE URINAL

TECHNICAL FIELD

The present invention relates to a portable urinal.

BACKGROUND ART

In general, a urinal is a toilet which is used for receiving urine which is stored in the bladder as a solution that accumulates and stores various wastes generated in the body as a result of human metabolism in the form of an aqueous solution and then excreted from the body when the amount thereof reaches a certain limit.

Conventional urinals are divided into women's urinals and men's urinals, and a toilet stool which is fixedly installed in each partition of the toilet is used for the women's urinals as it is, and a separate wall-mounted type or vertical urinal fixedly installed to the toilet is used as the men's urinals.

However, since the conventional urinals are fixed in the toilet, there is a problem in that it is impossible to be used under driving, during the operation of the store during the mountain or long distance trip, or during outdoor gathering.

For example, if a user feels urgent urination when a road is blocked while driving or the user can not find a toilet, the user feels a lot of trouble. In the case of women, even if the user finds a public restroom, the user has to wait in line for a toilet, and the user feels unpleasant because the user uses the same toilet stool used by others in aircrafts, trains, ships, etc. In the case of a single store, if the user feels urgent urination while the store is operating, the user feels difficulty because the user can not leave the store. There is a problem in that the user can not go to the toilet even if the user feels urgent urination in a situation where it is difficult to act. There is a problem in that if the user feels urgent urination while traveling in an unfamiliar area, the user feels difficult because the user can not find a toilet. It is difficult to go to the toilet in an outdoor meeting place where people gather by a group.

In addition, people who have diseases such as incontinence, prostate, and residual urine have a problem of always living in tension to find the toilet.

DISCLOSURE

Technical Problem

An object of the present invention is to provide a portable urinal capable of handling urgent urination or urination without using the conventional toilet.

Technical Solution

To achieve the object, an embodiment of the present invention provides a potable urinal including: a moisture solidification layer containing a super absorbent polymer; a plate-shaped support member supporting the moisture solidification layer and having a hollow portion; and a shape retaining wire retaining the plate-shaped support member in the form of an alphabet "C".

The portable urinal may further include a first absorbent nonwoven fabric covering the plate-shaped support member and having a slit formed at a portion corresponding to the hollow portion.

The first absorbent nonwoven fabric may be attached to the plate-shaped support member.

The portable urinal may further include a vinyl member covering an opposite side of the moisture solidification layer to a side facing the plate-shaped support member and having an edge portion attached to the edge portion of the first absorbent nonwoven fabric.

The vinyl member may be a biodegradable vinyl.

The portable urinal may further include a second absorbent nonwoven fabric entirely covering the moisture solidification layer inside the vinyl member.

A side of the second absorbent nonwoven fabric facing the vinyl member may be attached to the vinyl member.

The slit may have a cross shape.

The plate-shaped support member may have a horizontally elongated shape, the hollow portion may have a horizontally elongated elliptic shape, the plate-shaped support member may include a left portion and a right portion placed on the left and right sides with respect to the hollow portion, and a front portion and a back portion placed on the front and back portions with respect to the hollow portion. In the case, the portable urinal may further include a reinforcing member reinforcing the left portion and the right portion of the plate-shaped support member.

The shape retaining wire may have a single closed curve in the form of covering the plate-shaped support member and be provided along the edge of the plate-shaped support member.

The shape retaining wire may be made of an elastic material having a restoring force.

As an example, the shape retaining wire may include a central portion positioning the hollow portion therebetween; and both end portions extending to both ends of the central portion, respectively, to position the central portion therebetween, in which the central portion and the both end portions may be formed as one body.

As another example, the shape retaining wire may include a central portion positioning the hollow portion therebetween; both end portions extending to both ends of the central portion, respectively, to position the central portion therebetween; and a rotating portion providing rotatably each of the both end portions with respect to the central portion.

As yet another example, the shape retaining wire may include a central portion positioning the hollow portion therebetween; both end portions extending to both ends of the central portion, respectively, to position the central portion therebetween; and a slider portion providing slidably each of the both end portions with respect to the central portion.

Advantageous Effects

As described above, the portable urinal according to the embodiment of the present invention may have the following effects.

According to the embodiment of the present invention, since a technical configuration including the moisture solidification layer, the plate-shaped support member, and the shape retaining wire is provided, children and adults of all ages which can use the hands may handle urgent urination or urination by carrying and wearing the technical configuration without using the conventional toilet. In particular, since the state in which the technical configuration is in contact with the body may be maintained by the shape retaining wire, the users may urinate without leakage of urine without taking down clothes such as pants, so that the technical configuration may be used irrespective of place, environment, posture and the like. In addition, since the urine is solidified in the moisture solidification layer, the odor due to the urine odor may be prevented. Furthermore, due to the spread of the portable urinal, it is possible to reduce the number of public toilets and improve the environment.

Further, according to the embodiment of the present invention, since the technical configuration further including the first absorbent nonwoven fabric having the slit is provided, the first absorbent nonwoven fabric is lifted up by the slit to wipe the skin with the urine after use.

Further, according to the embodiment of the present invention, since the biodegradable vinyl is used, environmental pollution can be minimized.

DESCRIPTION OF DRAWINGS

FIG. 1 is a plan view schematically illustrating a portable urinal according to an embodiment of the present invention.

FIG. 2 is a cross-sectional view of the portable urinal of FIG. 1 taken along line II-II.

FIG. 3 is a view schematically illustrating a state in which urine is absorbed into the portable urinal of FIG. 1.

FIG. 4 is a perspective view schematically illustrating an example of a shape retaining wire in the portable urinal of FIG. 1.

FIG. 5 is a perspective view schematically illustrating another example of the shape retaining wire.

FIG. 6 is a perspective view schematically illustrating yet another example of the shape retaining wire.

MODES OF THE INVENTION

Hereinafter, embodiments of the present invention will be described in detail with reference to the accompanying drawings so as to easily implement those with ordinary skill in the art to which the present invention pertains. However, the present invention may be embodied in many different forms and are limited to embodiments described herein.

FIG. 1 is a plan view schematically illustrating a portable urinal according to an embodiment of the present invention, FIG. 2 is a cross-sectional view of the portable urinal of FIG. 1 taken along line II-II, and FIG. 3 is a view schematically illustrating a state in which urine is absorbed into the portable urinal of FIG. 1.

FIG. 4 is a perspective view schematically illustrating an example of a shape retaining wire in the portable urinal of FIG. 1, FIG. 5 is a perspective view schematically illustrating another example of the shape retaining wire, and FIG. 6 is a perspective view schematically illustrating yet another example of the shape retaining wire.

A portable urinal 100 according to an embodiment of the present invention includes a moisture solidification layer 110, a plate-shaped support member 120, and a shape retaining wire W, as illustrated in FIGS. 1 to 6. Hereinafter, respective components will be described in detail with reference to FIGS. 1 to 6.

The moisture solidification layer 110 is a component for directly absorbing urine to be urinated as illustrated in FIGS. 2 and 3 and contains a super absorbent polymer (SAP) 111. Here, as it is known, the SAP 111 may absorb water several tens to several hundreds times as much as its own weight, and has a characteristic in which water is not emitted even under a tolerable pressure. Accordingly, if the moisture solidification layer 110 is formed by adjusting the amount of the SAP 111 in accordance with the maximum value of a once-urine volume, the urine to be urinated may be absorbed and solidified.

The plate-shaped support member 120 is a component that supports the moisture solidification layer 110, as illustrated in FIGS. 1 to 3. Accordingly, when the user holds the portable urinal 100 of the present invention and inserts the portable urinal 100 of the present invention between the crotches, the shape of the portable urinal 100 of the present invention is retained by the plate-shaped support member 120, and thus the moisture solidification layer 110 may be smoothly inserted between the crotches without being crumpled, so that anyone who can use the hands may wear the portable urinal anytime and anywhere. For example, as the plate-shaped support member 120, a hard paper such as a cardboard or a material having good elasticity such as plastic may be used.

As illustrated in FIGS. 1 to 3, since a hollow portion 121 is opened in the center of the plate-shaped support member 120, even if the plate-shaped support member 120 is present, the user's urine may be smoothly guided to the moisture solidification layer 110 through the hollow portion 121.

The shape retaining wire W is a component for closely bringing the portable urinal 100 of the present invention into contact with the user's body so as to prevent the portable urinal 100 of the present invention from being removed. The shape retaining wire W may have a curved shape in the form of an alphabet "C" as illustrated in FIG. 4. Accordingly, since the plate-shaped support member 120 may be retained in the form of "C" by the shape retaining wire W, when the portable urinal 100 of the present invention is inserted between the user's crotches, the portable urinal 100 of the present invention may be in contact with the user's body by covering the user's crotches and pelvis by the shape retaining wire W. Ultimately, it is possible to prevent the urine from being leaked between the portable urinal 100 of the present invention and the user's body.

Furthermore, the shape retaining wire W has a single closed curve in the form of covering the plate-shaped support member 120 as illustrated in FIG. 4, and may be provided on the edge of the plate-shaped support member 120 as illustrated in FIGS. 1 to 3.

The shape retaining wire W may be made of an elastic material having a restoring force. Accordingly, the shape retaining wire W may be stretched or contracted to be in contact with the user's body in accordance with the user's body size.

Such a shape retaining wire W may have three examples as illustrated in FIGS. 4 to 6. As an example, as illustrated in FIG. 4, the shape retaining wire W1 may include a central portion 172 positioning the hollow portion 121 of the plate-shaped support member 120 therebetween and both end portions 172 extending to both ends of the central portion 171, respectively, to position the central portion 171 therebetween, and the central portion 171 and the both end portions 172 may be formed as a single body.

As another example, as illustrated in FIG. 5, a shape retaining wire W2 may include a central portion 271 positioning the hollow portion 121 of the plate-shaped support member 120 therebetween, both end portions 272 extending to both ends of the central portion 271, respectively, to position the central portion 271 therebetween, and rotating portions 273 providing rotatably the both end portions 272 with respect to the central portion 271, respectively. Accordingly, the both end portions 272 corresponding to wing portions may be folded and unfolded toward the central portion 271 by the rotating portions 273, so that the both end portions 272 may be stored while folded before and after use by reducing the volume, and may be unfolded and used in use. Here, the rotating portions 273 may be implemented through a hinge shaft 273a or the like.

As yet another example, as illustrated in FIG. 6, a shape retaining wire W3 may include a central portion 371 positioning the hollow portion 121 of the plate-shaped support member 120 therebetween, both end portions 372 extending to both ends of the central portion 371, respectively, to position the central portion 371 therebetween, and a slider portion 373 providing slidably the both end portions 372 with respect to the central portion 371, respectively. Accordingly, the both end portions 372 corresponding to the wing portions may be inserted into and removed from the central portion 372 by the slider portion 373, so that the both end portions 272 may be stored while inserted before and after use by reducing the volume, and may be removed and used in use. Here, the slider portion 373 may be implemented through inlet and outlet holes 373a or the like.

Accordingly, since the portable urinal 100 including the moisture solidification layer 110, the plate-shaped support member 120, and the shape retaining wire W is provided, children and adults of all ages which can use the hands may handle urgent urination or urination by carrying and wearing the portable urinal 100 without using the conventional toilet. In particular, since the state in which the portable urinal 100 is in contact with the body may be maintained by the shape retaining wire W, the users may urinate without leakage of urine without taking down clothes such as pants, so that the portable urinal may be used irrespective of place, environment, posture and the like. In addition, since the urine is solidified in the moisture solidification layer 110, the odor due to the urine odor may be prevented. Furthermore, due to the spread of the portable urinal 100 of the present invention, it is possible to reduce the number of public toilets and improve the environment.

In addition, the portable urinal 100 according to the embodiment of the present invention may further include a first absorbent nonwoven fabric 130, as illustrated in FIGS. 1 to 3. The first absorbent nonwoven fabric 130 may cover the plate-shaped support member and a slit 131 may be formed at a portion corresponding to the hollow portion 121.

Accordingly, during the urination, the first absorbent nonwoven fabric 130 is moved toward the moisture solidification layer 110 by the pressure of the urine so that the urine may be smoothly moved to the moisture solidification layer 110 through the slit 131 while the slit 131 is opened, and the urine that is partially bounced back from the moisture solidification layer 110 may be blocked from the first absorbent nonwoven fabric 130. In addition, as the volume of the moisture solidification layer 110 absorbing the urine is expanded, when the user removes the portable urinal 100 of the present invention from the body while the first absorbent nonwoven fabric 130 is lifted up toward the skin by the expanding force and the slit 131, the urine coming into contact with the skin may be wiped by the first absorbent nonwoven fabric 130 lifted up.

Further, as illustrated in FIG. 1, the slit 131 may have a cross shape. Accordingly, during the urination, the slit 131 may be sufficiently opened in a cross shape, and the urine which is partially splashed in the moisture solidification layer 110 may be blocked by the first absorbent nonwoven fabric 130. As the volume of the moisture solidification layer 110 is expanded, four portions of the first absorbent nonwoven fabric 130 are lifted up toward the skin by the expanding force and the cross-shaped slit, so that the urine-stained skin may be sufficiently wiped.

In particular, the first absorbent nonwoven fabric 130 may be attached to the plate-shaped support member through an adhesive (not illustrated). Here, the adhesive may be supplied in a hot melt type on a manufacturing line.

In addition, the portable urinal 100 according to the embodiment of the present invention may further include a vinyl member 140, as illustrated in FIGS. 2 to 3. The vinyl member 140 covers an opposite side of the moisture solidification layer 110 to a side facing the plate-shaped support member 120 and an edge portion of the vinyl member 140 may be attached to an edge portion of the first absorbent nonwoven fabric 130 through an adhesive (not illustrated). Accordingly, the moisture solidification layer 110 may be covered by the vinyl member 140 to minimize the leakage of urine odor and the like before removing after using.

Particularly, the adhesive may be supplied in a hot melt type on a manufacturing line. In addition, as the vinyl member 140, a biodegradable vinyl may be used. The biodegradable vinyl is degraded after about 45 days to minimize environmental pollution.

In addition, the portable urinal 100 according to the embodiment of the present invention described above may further include a second absorbent nonwoven fabric 150, as illustrated in FIGS. 1 to 3. The second absorbent nonwoven fabric 150 may cover entirely the moisture solidification layer 110 inside the vinyl member 140. Accordingly, it is possible to prevent the super absorbent polymer contained in the moisture solidification layer 110 from being removed to the outside through the silt 131 of the first absorbent nonwoven fabric 130.

In particular, the side of the second absorbent nonwoven fabric 150 facing the vinyl member 140 may be attached to the vinyl member 140 through an adhesive (not illustrated). Here, the adhesive may be supplied in a hot melt type on a manufacturing line.

Further, as illustrated in FIG. 1, the plate-shaped support member 120 may have a horizontally elongated shape, and the hollow portion 121 may have a horizontally elongated elliptical shape. The plate-shaped support member 120 may include a left portion LP and a right portion RP placed on the left and right sides with respect to the hollow portion 121, and a front portion FP and a back portion BP placed on the front and back sides with respect to the hollow portion 121.

In this case, the portable urinal 100 according to the embodiment of the present invention may further include a reinforcing member 160 for reinforcing the left portion LP or the right portion RP of the plate-shaped support member 120 as illustrated in FIG. 1. Accordingly, when the user holds the portable urinal 100 of the present invention and inserts the portable urinal 100 of the present invention between the crotches, the shape of the portable urinal 100 of the present invention is retained well by the plate-shaped support member 120 and the reinforcing member 160, and thus the moisture solidification layer 110 may be smoothly inserted between the crotches without being crumpled. For example, the reinforcing member 160 may be a rigid paper.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

INDUSTRIAL AVAILABILITY

The present invention has the industrial availability capable of handling urgent urination or urination while

EXPLANATION OF REFERENCE NUMERALS AND SYMBOLS

| | |
|---|---|
| 100: Portable urinal | 110: Moisture solidification layer |
| 111: Super absorbent polymer | 120: Plate-shaped support member |
| 121: Hollow portion | 130: First absorbent nonwoven fabric |
| 131: Slit | 140: Vinyl member |
| 150: Second absorbent nonwoven fabric | 160: Reinforcing member |
| W1, W2, W3: Shape retaining wire | 172, 272, 372: Both end portions |
| | 273a: Hinge shaft |
| 171, 271, 371: Central portion | 373a: inlet and outlet holes |
| 273: Rotating portion | |
| 373: Slider portion | |

The invention claimed is:

1. A portable urinal comprising:
   a moisture solidification layer containing a super absorbent polymer;
   a plate-shaped support member supporting the moisture solidification layer and having a hollow portion; and
   a shape retaining wire retaining the plate-shaped support member in a form of an alphabet "C",
   wherein the shape retaining wire is provided along an edge of the plate-shaped support member, and wherein the shape retaining wire includes:
   a pair of central portions positioning the hollow portion therebetween;
   a pair of end portions extending to a pair of ends of the central portions, respectively, to position the central portions therebetween; and
   a slider portion providing slidably each of the end portions with respect to the central portions.

2. The portable urinal of claim 1, further comprising:
   a first absorbent nonwoven fabric covering the plate-shaped support member and having a slit formed at a portion corresponding to the hollow portion.

3. The portable urinal of claim 2, further comprising:
   a vinyl member covering an opposite side of the moisture solidification layer to a side facing the plate-shaped support member and having an edge portion attached to an edge portion of the first absorbent nonwoven fabric.

* * * * *